United States Patent
Heo

(10) Patent No.: US 9,986,955 B2
(45) Date of Patent: *Jun. 5, 2018

(54) INTRA ORAL SENSOR DEVICE

(71) Applicants: Rayence Co., Ltd., Gyeonggi-do (KR); VATECH EWOO Holdings Co., Ltd., Gyeonggi-do (KR)

(72) Inventor: Sung-Kyn Heo, Gyeonggi-do (KR)

(73) Assignees: Rayence Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/502,599

(22) PCT Filed: Aug. 10, 2015

(86) PCT No.: PCT/KR2015/008348
§ 371 (c)(1),
(2) Date: Feb. 8, 2017

(87) PCT Pub. No.: WO2016/022006
PCT Pub. Date: Feb. 11, 2016

(65) Prior Publication Data
US 2017/0224295 A1    Aug. 10, 2017

(30) Foreign Application Priority Data
Aug. 8, 2014 (KR) .................. 10-2014-0102295

(51) Int. Cl.
*A61B 6/00* (2006.01)
*A61B 6/14* (2006.01)

(52) U.S. Cl.
CPC .................................. *A61B 6/145* (2013.01)

(58) Field of Classification Search
None
See application file for complete search history.

(56) References Cited

U.S. PATENT DOCUMENTS

| 4,734,034 A | 3/1988 | Maness et al. |
| 4,856,993 A | 8/1989 | Maness et al. |

(Continued)

FOREIGN PATENT DOCUMENTS

| EP | 1699232 A2 | 9/2006 |
| EP | 2213238 A1 * | 4/2010 |

(Continued)

OTHER PUBLICATIONS

Korean Intellectual Property Office, International Search Report of International Application No. PCT/KR2015/008348, dated Nov. 20, 2015.

(Continued)

*Primary Examiner* — Hoon Song
(74) *Attorney, Agent, or Firm* — IP Legal Services, LLC

(57) ABSTRACT

The present invention provides an oral sensor device comprising: a sensor assembly which is bendable and generates an electrical signal by detecting an X-ray; and a window cover comprising a base portion and a side wall, the base portion being positioned on the front of a sensor panel with respect to the traveling direction of the X-ray, and covering the sensor panel, and the side wall protruding toward the rear from the lateral side of the edge of the base portion so as to cover the lateral surface of the sensor panel, and having a plurality of grooves formed on at least a part thereof.

11 Claims, 5 Drawing Sheets

(56) References Cited

U.S. PATENT DOCUMENTS

| | | | |
|---|---|---|---|
| 6,042,267 A | * | 3/2000 | Muraki ............ G01T 1/2018 348/E5.086 |
| 2003/0031296 A1 | | 2/2003 | Hoheisel |
| 2006/0028546 A1 | | 2/2006 | Kokkaliaris et al. |
| 2006/0067462 A1 | | 3/2006 | Hack |
| 2006/0262461 A1 | | 11/2006 | Wood |
| 2007/0053498 A1 | | 3/2007 | Mandelkern et al. |
| 2009/0034687 A1 | | 2/2009 | Ayraud |
| 2010/0072379 A1 | | 3/2010 | Nishino et al. |
| 2010/0074401 A1 | | 3/2010 | Kayzerman |
| 2011/0013745 A1 | | 1/2011 | Zeller et al. |
| 2012/0291554 A1 | | 11/2012 | Baba et al. |

FOREIGN PATENT DOCUMENTS

| | | |
|---|---|---|
| JP | 2006-043465 A | 2/2006 |
| JP | 2006-521130 A | 9/2006 |
| JP | 2011-075390 A | 4/2011 |
| JP | 2013-015347 A | 1/2013 |
| KR | 20-0303670 Y1 | 2/2003 |
| KR | 20-0396821 Y1 | 9/2005 |
| KR | 20-2009-0001520 U | 2/2009 |
| KR | 10-2014-0061177 A | 5/2014 |
| KR | 10-2014-0067257 A | 6/2014 |
| WO | 2009/138331 A1 | 11/2009 |

OTHER PUBLICATIONS

Korean Intellectual Property Office, Written Opinion of International Application No. PCT/KR2015/008348, dated Nov. 20, 2015.
Korean Intellectual Property Office, International Search Report of International Application No. PCT/KR2015/004658, dated Aug. 13, 2015.
Korean Intellectual Property Office, International Search Report of International Application No. PCT/KR2015/008347, dated Nov. 6, 2015.
Korean Intellectual Property Office, International Search Report of International Application No. PCT/KR2015/008349, dated Nov. 23, 2015.
Korean Intellectual Property Office, Written Opinion of International Application No. PCT/KR2015/008349, dated Nov. 23, 2015.
Korean Intellectual Property Office, Written Opinion of International Application No. PCT/KR2015/008347, dated Nov. 6, 2015.
European Patent Office, Extended European Search Report of EP Patent Application No. 15829636.8, dated Apr. 18, 2018.

* cited by examiner

INTRA ORAL SENSOR DEVICE

CROSS REFERENCE TO RELATED APPLICATIONS

This application is a National Stage Patent Application of PCT International Patent Application No. PCT/KR2015/008348 (filed on Aug. 10, 2015) under 35 U.S.C. § 371, which claims priority to Korean Patent Application No. 10-2014-0102295 (filed on Aug. 8, 2014), the teachings of which are incorporated herein in their entireties by reference.

TECHNICAL FIELD

The present invention relates to an intra oral sensor device, and more particularly, to an intra oral sensor device, which is inserted into the mouth for intra-intra oral X-ray scans and is bendable within a certain range by physical force toward an intra-intra oral structure and repulsive force in relation to arrangement of the structure.

BACKGROUND ART

In the conventional approach for intra-intra oral X-ray scans to obtain X-ray images of teeth and surrounding tissues in the mouth, a film-based method is used.

The film-based method may cause the images distortion due to film's excessive twist in the mouth and is more likely to lead to image distortions, and is inefficient in terms of time and expense because the film on which images have been captured needs to be developed and stored. To address the problem, a digital intra oral sensor device is being widely used these days.

The digital intra oral sensor device typically consists of rigid parts, making it inflexible. Although image distortion is less likely to occur during the intra-intra oral scan, this inflexibility gives the patient a strong unfamiliar or painful feeling. For example, in the case of taking an intra-intra oral X-ray scan to obtain X-ray images of intra-intra oral structures, such as teeth and surrounding tissues, the intra oral sensor device is put in the mouth and X-rays are radiated from an external X-ray source to scan the structures located between the intra oral sensor device and the external X-ray source. The intra oral sensor device pressurizes and adheres closely to the intra-intra oral structures to obtain more accurate X-ray images, which gives the patient a stronger or more painful foreign sensation.

Accordingly, an urgent need exists for the development of a digital intra oral sensor device to solve the discomfort of the patient, and in this regard, an intra oral sensor device bendable to a certain extent, i.e., bendable to a limited extent, is being discussed in the related industry.

At present, however, only the abstract concept of the 'bendable' property is being discussed, and no specific research into an intra oral sensor device having a readily bendable property is currently being conducted.

DISCLOSURE

Technical Problem

Accordingly, the present invention has been made keeping in mind the above problems occurring in the prior art, and an object of the present invention is to provide an intra oral sensor device, which is inserted into the mouth for intra-intra oral X-ray scans and is bendable within a certain range upon the application of physical force toward an intra-intra oral structure and repulsive force in relation to the arrangement of the structure, thereby relieving the foreign feeling and pain of the patient.

Technical Solution

In accordance with an aspect of the present invention, disclosed is an intra oral sensor device including a bendable sensor assembly for detecting an X-ray and generating an electric signal; and a window cover located in front of the sensor panel with respect to the direction of X-ray propagation, and having a base part covering the sensor panel, and side walls protruding from edges of the base part to cover the sides of the sensor panel and having grooves formed in at least a part of the side walls.

The grooves may be formed in the side walls, arranged along the major axis of the window cover, and the intervals between the grooves may become narrower from the center of the side wall to either end thereof. Gaps may be formed between neighboring side walls at the edges of the base part. Each groove may include a first groove part extending down from the top of the side wall and having first width, and a second groove part located below the first groove part, at least a part of the second groove part having a second width greater than the first width. The second groove part may be shaped like a circle. The window cover may be formed of a FRP or a flexible glass material. The sensor assembly may include a sensor panel for detecting the X-ray and generating the electric signal, a circuit panel located behind and connected to the sensor panel to deliver the electric signal, and an elasticity adjustment member located between the sensor panel and the circuit panel and formed of an elastic material having elasticity greater than that of the sensor panel and the circuit panel. The intra oral sensor device may further include a protective cover to cover the sensor panel from behind the sensor panel with respect to the direction of X-ray propagation; and a mold housing to wrap up the exterior of the intra oral sensor device. The mold housing may be formed of a material having a shore hardness of A 30 to 50. The mold housing may be formed of a silicon or urethane material.

Advantageous Effects

An intra oral sensor device in accordance with the present invention uses a window cover to contain and protect a bendable sensor assembly as well as maximize the property of limited flexibility at its edges against external force during intra-intra oral X-ray scans. Accordingly, a bendable intra oral sensor device may be implemented to prevent the breakage of a main part, that is, the sensor assembly, especially a sensor panel, minimize the distortion of images, and relieve the patient's discomfort to a significant extent.

For this, grooves may be formed in the wall of the window cover to control the flexibility, thereby minimizing distortion of images during an intra-intra oral scan and more effectively relieving the patient's discomfort.

Furthermore, a soft mold housing may be used to cover the exterior of the intra oral sensor device, thereby significantly relieving the discomfort felt by the patient during a scan.

Moreover, the mold housing may be extended to wrap a part of a transmission cable, thereby reliably fixing the connection between the transmission cable and the intra oral sensor device.

Consequently, according to the present invention, an intra oral sensor device having a property of limited flexibility that helps minimize image distortion may be efficiently implemented, and in addition, may reliably protect a connection part between the transmission cable and a printed circuit board (PCB) and minimize the discomfort felt by the patient.

BEST MODE

Embodiments of the present invention will now be described in detail with reference to accompanying drawings.

Figure 1:
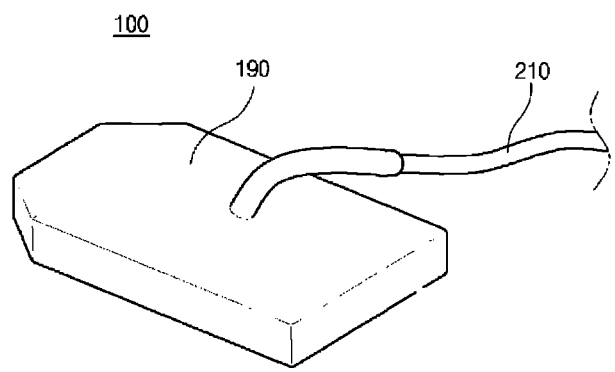
FIG. 1 is a perspective view schematically illustrating an intra oral sensor device, according to an embodiment of the present invention.
Figure 2:
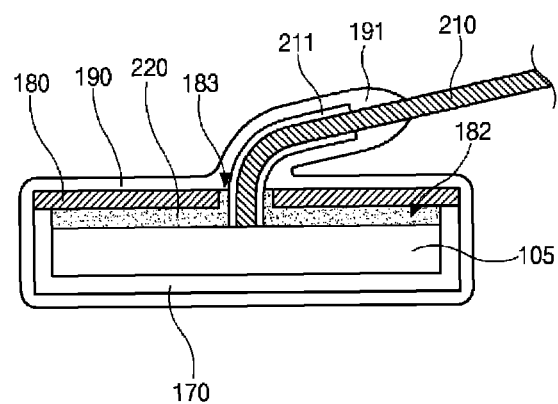
FIG. 2 is a cross-sectional view schematically illustrating an intra oral sensor device, according to an embodiment of the present invention.

FIG. 1 is a perspective view schematically illustrating an intra oral sensor device according to an embodiment of the present invention, and FIG. 2 is a cross-sectional view schematically illustrating an intra oral sensor device according to an embodiment of the present invention.

Referring to FIGS. 1 and 2, an intra oral sensor device 100 in accordance with an embodiment of the present disclosure may include a sensor assembly 105 for detecting X-rays and generating electric signals, a window cover 170 located in front of the sensor assembly 105 (i.e. on the side onto which X-rays are incident), a protection cover 180 located behind the sensor assembly 105, and a mold housing 190 to wrap the exterior of the intra oral sensor device 100.

In the following, the respective components will be described in detail.

Figure 3:
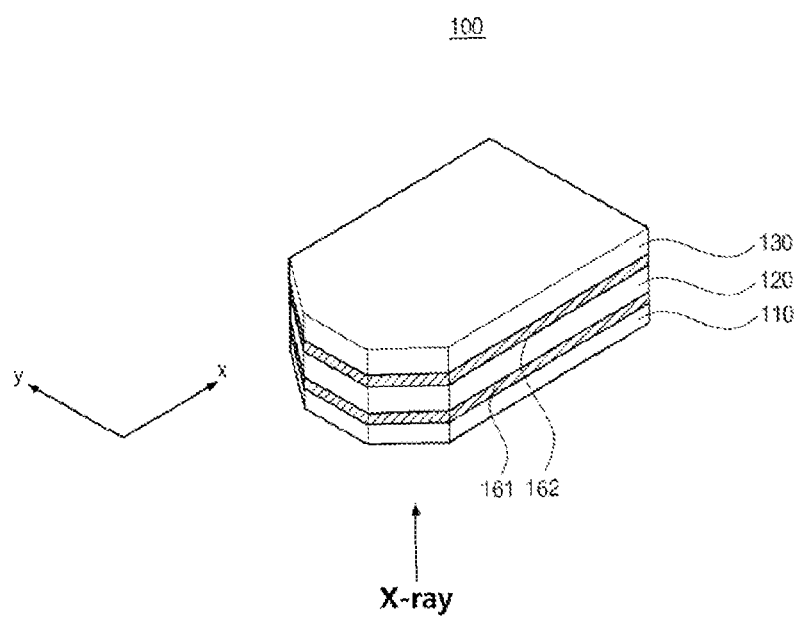
FIG. 3 is a cross-sectional view schematically illustrating a sensor assembly, according to an embodiment of the present invention.

The sensor assembly 105 will be described in more detail in connection with FIG. 3. FIG. 3 schematically illustrates a sensor assembly according to an embodiment of the present invention.

Referring to FIG. 3, the sensor assembly 105 may include a sensor panel 110, an elasticity adjustment member 120, and a printed circuit board (PCB) 130. The sensor panel 100, elasticity adjustment member 120, and PCB 130 may be arranged in the direction of X-ray propagation, without being limited thereto.

In the sensor panel 110, a number of pixels are arranged in rows and columns to form a matrix in an effective area, i.e., an active area for image acquisition. A photoelectric transducer element, such as a photo diode and a switching element, are arranged for each pixel for converting incident light to an electric signal and transmitting the electric signal. In the meantime, although not shown, pads may be formed on one side of the sensor panel 110 to output the electric signal, and the switching element may be implemented as a complementary metal-oxide semiconductor (CMOS) transistor or a thin film transistor (TFT).

To realize the bendable property of the intra oral sensor device 100, the sensor panel 100 may also be formed to be bendable, and for this, the sensor panel 110 may use a fragile substrate formed of e.g. semiconductor, ceramic, glass, or the like, which is 100 um thick or less, for example, 30 um to 70 um thick. With the substrate formed to this thickness, the sensor panel 110 may have the optimum bending strength.

To form the sensor panel 110 having this thickness, for example, a method for removing a certain thickness of material from the rear side of the substrate may be used. Specifically, on the other side, opposite the side on which the photoelectric transducer is formed, a process such as mechanical grinding, chemical polishing, plasma etching, etc. may be performed to form the substrate to the thickness described above.

In the meantime, for the sensor panel 110, a sensor panel using a direct conversion scheme for directly converting an incident X-ray to an electric signal, or a sensor panel using an indirect conversion scheme for converting an incident X-ray to a visible ray and then to an electric signal may be used.

Figure 4:
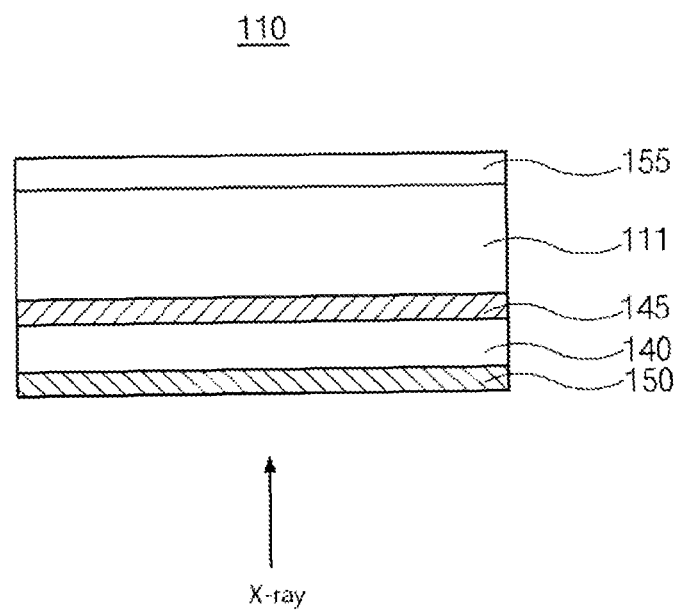
FIG. 4 is a plan schematically illustrating a sensor panel, according to an embodiment of the present invention.

If the sensor panel 110 of the indirect conversion scheme is used, referring to FIG. 4, showing a cross-sectional view of the sensor panel 100 in accordance with an embodiment of the present invention, a scintillator layer 140 for converting X-rays to visible rays may be formed on one side of a substrate 111 of the sensor panel 110, i.e., on the photoelectric transducer element.

Although FIG. 4 shows an example where the scintillator layer 140 is formed on the side of the sensor panel 110 on which X-rays are incident, the scintillator layer 140 may be formed on the side opposite the side on which the X-rays are incident in another example.

For example, the scintillator layer 140 may be adhered to the substrate 111 using an adhesive 145. Furthermore, on the scintillator layer 140, a protective film 150, which is transparent to radiation, may be formed to protect the scintillator layer 140. The adhesive 145 may use a very soft adhesive highly transparent to light, e.g., an Optically Clear Adhesive (OCA) film, and the protective film 150 may use a film of a resin material with high radiation transmittance and high humidity-blocking performance. For reference, the adhesive 145 of the OCA film may be 10 to 50 um thick, preferably 15 to 40 um thick, to relieve the brittleness of the substrate.

In the meantime, the scintillator layer 140 may use a CsI based scintillator, or Gadox (Gadox: $Gd_2O_2$: Tb)-based scintillator.

In an embodiment of the present invention, since the intra oral sensor device 100 is formed to have the bendable property, a Gadox-based scintillator may be more appropriately used than a CsI-based scintillator. Since the Gadox-based scintillator has a corpuscular structure, when the intra oral sensor device 100 is bent, the intra oral sensor device 100 is less likely to break, thereby avoiding defects. Furthermore, the scintillator layer 140 using Gadox has an advantage of being easily manufactured.

For reference, the scintillator layer 140 using Gadox may be 250 to 500 um thick, preferably 300 to 450 um thick in order to obtain sufficient intensity of radiation.

Moreover, a flexible layer 155 may be formed on the other side of the substrate 111 where the scintillator layer 140 is formed, and the flexible layer 155 may be formed of a flexible resin material, e.g., polyimide PI. The flexible layer 155 may have a thickness of, for example, 50 to 150 um, enough to relieve the brittleness of the sensor panel 100, especially the substrate 111, and to prevent breakage in the event of bending of the intra oral sensor device 100.

Turning back to FIG. 3, the PCB 130, which is a circuit panel, is located behind the sensor panel 110, and is electrically connected to one side of the sensor panel 110 in order to receive an electric signal generated by and received from the sensor panel 110 and to send out the electric signal.

As the PCB 130, a so-called "flexible PCB", made of a flexible material, may be used to realize the bendable property of the sensor assembly 110.

Figure 5:
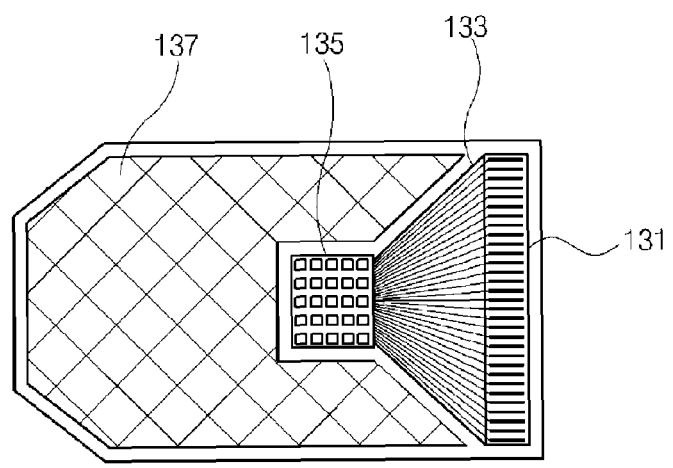
FIG. 5 is a perspective view schematically illustrating a printed circuit board (PCB), according to an embodiment of the present invention.

In this regard, referring to FIG. 5 showing a plan view schematically illustrating the PCB 130 in accordance with an embodiment of the present invention, a panel connection pad unit 131, a conductive wire pattern unit 133, and a cable connection pad unit 135 may be formed on the PCB 130.

As shown in FIG. 5, the panel connection pad unit 131 is formed on one side of the PCB 130, on which a number of pads are formed. The pads of the panel connection pad unit 131 are electrically connected to corresponding pads formed on one side of the sensor panel 110 by wire bonding, soldering, Anisotropic Conductive Film (ACF) or the like, for receiving an electric signal generated from the sensor panel 110.

In the conductive wire pattern unit 133, a number of wire patterns is formed to connect the panel connection pad unit 131 and the cable connection pad unit 135 located at either ends. One end of the wire pattern is connected to the panel connection pad unit 131 to deliver an electric signal, applied from the sensor panel 110, to the cable connection pad unit 135, which is connected to the other end of the wire pattern.

The cable connection pad unit 135 corresponds to an arrangement from which a transmission cable (see 210 of FIGS. 1 and 2) is connected to transmit electric signals to the outside. The transmission cable may be connected to the cable connection pad unit 135 in various ways, e.g. by soldering, using a connector, or using a conductive film.

In the meantime, a metal thin film 137, electrically isolated from the panel connection pad unit 131, conductive wire pattern unit 133, and cable connection pad unit 135, may be formed on one side of the PCB 130. The metal thin film 137 may be made of copper Cu, but is not limited thereto.

The metal thin film 137 may be formed on at least a part of an area exclusive of the area where the panel connection pad unit 131, conductive wire pattern unit 133, and cable connection pad unit 135 are formed.

The metal thin film 137 may serve as a means of grounding and electromagnetic interference (EMI) shielding for the PCB 130.

Furthermore, the metal thin film 137 may further serve as a means of controlling the bendable property of the PCB 130.

In this regard, without the metal thin film 137, there is a big difference in the extent of bending between an area where the panel connection pad unit 131, conductive wire pattern unit 133, and cable connection pad unit 135 are formed and the remaining area, but with the metal thin film 137 formed, the difference may be mitigated, making the overall extent of bending of the PCB 130 uniform for each area. The extent of bending of the PCB 130 may be adjusted by varying the material, formation area, thickness, etc., of the metal thin film 137.

In this embodiment of the present invention, a PCB 130 having a size corresponding to the sensor panel 110 is used. In another embodiment, the PCB 130 may be smaller than the sensor panel 110, and may be substantially formed of only the panel connection pad unit 131, conductive wire pattern unit 133, and cable connection pad unit 135. For reference, the thickness of the PCB 130 may be, without being limited thereto, 150 to 350 um thick, as long as it has elasticity equal to or less than that of the sensor panel 110.

Figure 6:
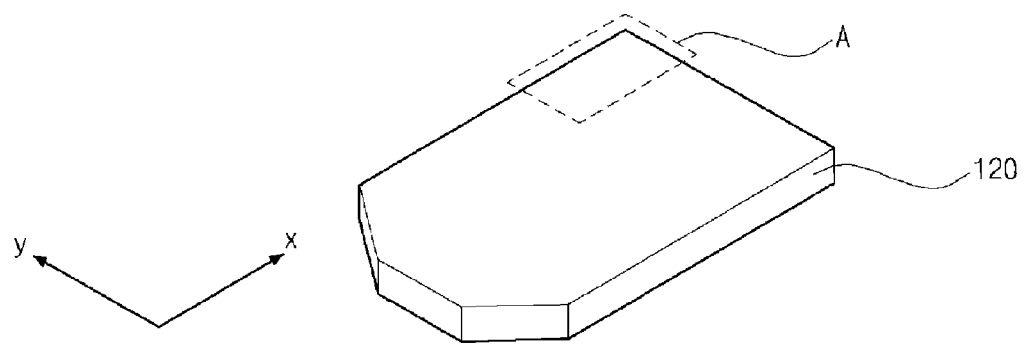
FIG. 6 is a perspective view schematically illustrating an elasticity adjustment member, according to an embodiment of the present invention.

FIG. 6 is a perspective view schematically illustrating the elasticity adjustment member 120, according to an embodiment of the present invention. It will be explained in conjunction with FIG. 3.

The elasticity adjustment member 120 may be located, for example, between the sensor panel 110 and the PCB 130, may have a shape corresponding to the sensor panel 110, and may be formed to cover the whole rear side of the sensor panel 110. The elasticity adjustment member 120 is made of an elastic material having elasticity equal to or more than that of the sensor panel 110 or the PCB 130. With this configuration, the elasticity adjustment member 120 may allow the sensor assembly 105 to have the bendable property and restorability while varying its bending extent within the limit of elasticity of the elasticity adjustment member 120 depending on the magnitude of external force as well as mitigate the brittleness of the sensor panel 110 to protect the sensor panel 1110 against bending of the sensor assembly 105 by controlling the extent of bending of the sensor panel 110 and the PCB 130, i.e. controlling the elasticity of the sensor panel 110 and PCB 130 to less than its bending extent, that is, to more than the elasticity of the elasticity adjustment member 120.

For example, although there may be a difference in elasticity between the components depending on their sizes, thicknesses, or the like, it is arbitrarily assumed that the sensor panel 110 and the PCB 130 have first elasticity and second elasticity, respectively, and given that the sensor panel 110 has the same structure and thickness as shown in FIG. 2, the first elasticity is typically equal to or greater than the second elasticity. Furthermore, the elasticity adjustment member 120 is made of an elastic material having third elasticity that is equal to or greater than the first elasticity, and accordingly, the elasticity adjustment member 120 may then serve for the sensor assembly 105 to be bendable within the elasticity limit of the elasticity adjustment member 120 by adjusting the elasticity of the sensor panel 110 and PCB 130 to the third elasticity or more and for the intra oral sensor device 100 to return to its original shape when the external force is eliminated after the intra oral sensor device 100 is bent within the elasticity limit of the elasticity adjustment member 120.

For this, the elasticity adjustment member 120 may use a resin material, particularly a complex mixture of more than two types of substances, and preferably a complex resin substance including a reinforcing material and a resin.

Furthermore, when superficially observed, the elasticity adjustment member 120 may have different bending properties in the first direction and the second direction, perpendicular to the first direction.

In this regard, for example, in the case where the sensor assembly 105 is shaped like a rectangle in an x-y plane, being longer along the x-axis than along the y-axis, the elasticity adjustment member 120 may be formed to have greater flexibility along the x-axis (as the major axis) than along the y-axis (as the minor axis). Even if the sensor assembly 105 is substantially shaped like a square, it may also be formed to have different bending properties with respect to the x- and y-axes.

With the bending properties, the sensor assembly 105 may be bent more easily along the major axis than along the minor axis, thereby effectively relieving discomfort of the patient wearing the sensor assembly 105 during an intra-intra oral scan.

In this regard, during the intra-intra oral scan, the patient may experience discomfort due to the edges of the sensor assembly 105, and in particular due to the ends of the major axis. Accordingly, forming the sensor assembly 105 to have greater flexibility along the major axis may significantly help relieve the discomfort felt by the patient.

Furthermore, since the flexibility along the x-axis, which is the major axis, is greater than that along the y-axis, which is the minor axis, torsion stress may be distributed into stresses along the x- and y-axes, and most of the torsion stress may be converted to stress along the x-axis to thus prevent breakage of the sensor panel 110, in particular the substrate 115.

As described above, the elasticity adjustment member 120 having different bending properties in different directions in the plane may be made of a complex resin material, e.g., fiber reinforced polymer (FRP) including a fiber reinforcing material. FRP is a substance in which inorganic fiber, such as glass fiber, carbon fiber, boron fiber, etc., or organic fiber such as aramid fiber, polyester fiber, Kevlar fiber, etc., is included as a reinforcing substance in a thermoset resin, such as unsaturated polyester, epoxy, phenol, polyimide, etc., or a thermoplastic resin, such as polyamide, polycarbonate, ABS, PBT, PP, SAN, etc.

The elasticity adjustment member 120 will be described in more detail in connection with FIG. 7.

Figure 7:
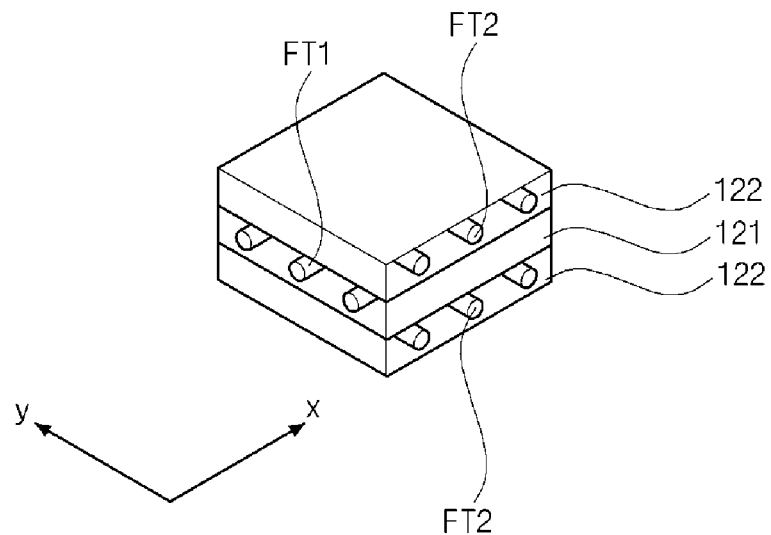
FIG. 7 is an expanded view of part "A" of FIG. 6 schematically illustrating a part of the elasticity adjustment member, according to an embodiment of the present invention.

FIG. 7 is an expanded view of part 'A' of FIG. 6, schematically illustrating a part of the elasticity adjustment member 120, which is a cross-section of the elasticity adjustment member 120.

Referring to FIG. 7, in the elasticity adjustment member 120, a first thread layer 121, on which first threads (FT1) are arranged in a first direction, the direction of the x-axis, and a second thread layer 122, on which second threads (FT2) are arranged in a second direction, the direction of the y-axis, are alternately arranged in the thickness direction while being impregnated in the resin substance. The first and second threads FT1 and FT2 may each be formed by gathering and weaving the aforementioned fiber in one direction.

Especially, in FIG. 7, the number of first thread layers 121 formed along the x-axis, the major axis, is less than the number of second thread layers 122 formed along the y-axis, the minor axis, and FIG. 7 shows an example where one first thread layer 121 and two second thread layers 122 are arranged, for convenience of explanation. The first and second thread layers FT1 and FT2 are made of a carbon material, and the elasticity adjustment member 120 in accordance with an embodiment of the present invention may use CFRP.

As such, with the first thread layers 121 arranged along the major axis in a smaller number than the number of second thread layers 122 arranged along the minor axis, the direction of the major axis has relatively low elasticity, i.e., high flexibility, while the direction of the minor axis has relatively high elasticity, i.e., low flexibility.

The ratio of elasticity in the direction of the major axis to that of the minor axis is approximately 1:1.5 to 1:6. The elasticity adjustment member 120 may be formed to a thickness of about 200 to 400 um. In the case where the elasticity adjustment member 120 has a thickness of 300 um, the elasticity adjustment member 120 may be formed to have elasticity in the direction of the major axis with 1,000 to 30,000 Mpa of bending strength and in the direction of the minor axis with 1,500 to 180,000 Mpa of bending strength, which also corresponds to the thickness of 200 to 400 um.

With the different number of thread layers 121, 122 arranged in alternate directions relative to each other in the form described above, an elasticity adjustment layer 120 having higher flexibility along the major axis than along the minor axis may be implemented.

Figure 8:
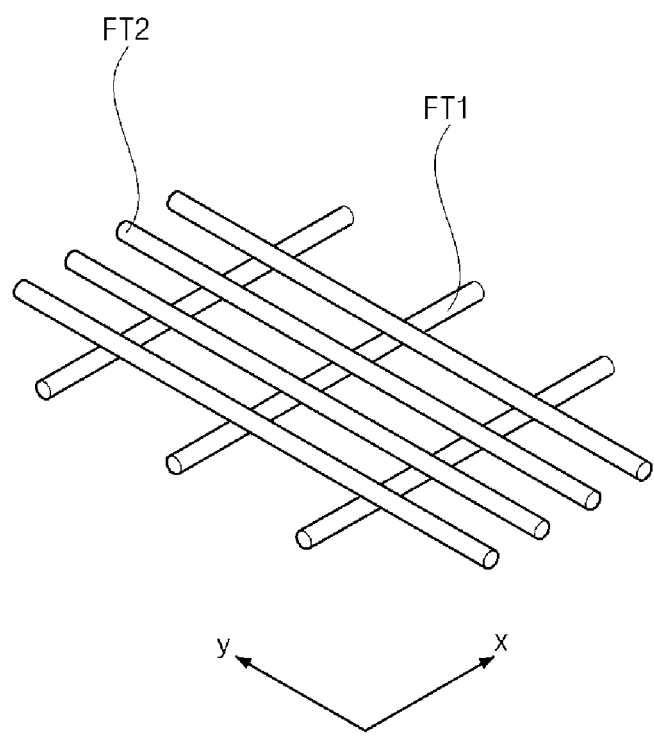
FIG. 8 is a partially expanded perspective view schematically illustrating a part of the elasticity adjustment member, according to another embodiment of the present invention.

FIG. 8 is a partially expanded perspective view schematically illustrating part of the elasticity adjustment member 120 according to another embodiment of the present invention, wherein the FT1 arranged in the first direction, i.e. along the x-axis, and the FT2 arranged in the second direction, i.e. along the y-axis, are impregnated in the resin substance while alternating with each other, and especially, the density of FT1 arranged along the x-axis, i.e. the major axis, is lower than the density of FT2 arranged along the y-axis, i.e. the minor axis, that is, the arrangement interval of FT1 is wider than the arrangement interval of FT2. The first and second threads FT1 and FT2 are made of a carbon material, and the elasticity adjustment member 120 in accordance with an embodiment of the present invention may use CFRP.

As such, with the density of FT1 in the direction of the major axis lower than that of FT2 in the direction of the minor axis, the direction of the major axis has relatively low elasticity, i.e. high flexibility, while the direction of the minor axis has relatively high elasticity, i.e. low flexibility.

Similar to what is described above, the ratio of elasticity of the major axis to elasticity of the minor axis may be approximately 1:1.5 to 1:6. The elasticity adjustment member 120 may be formed to a thickness of about 200 to 400 um. In the case where the elasticity adjustment member 120 has a thickness of 300 um, the elasticity adjustment member 120 may be formed to have elasticity in the direction of the major axis with 1,000 to 30,000 Mpa of bending strength and in the direction of the minor axis with 1,500 to 180,000 Mpa of bending strength, and the same is true for the thickness of 200 to 400 um.

With the different densities of FT1 and FT2 alternating with each other as described above, an elasticity adjustment layer 120 having higher flexibility along the major axis than along the minor axis may be implemented.

In the meantime, referring to FIG. 3, the elasticity adjustment member 120 may be combined with the sensor panel 110 and the PCB 130, located in front and back of the elasticity adjustment member 120, respectively, using adhesives 161, 162. For convenience of explanation, the adhesive 161 between the elasticity adjustment member 120 and the sensor panel 110 is called a first adhesive 161, and the adhesive 162 between the elasticity adjustment member 120 and the PCB 130 is called a second adhesive 161.

The first and second adhesives have good softness and may, by way of example, be optically clear adhesives (OCAs), without being limited thereto.

With the use of the first and second adhesives 161 and 162 having good softness, inter-layer stress produced when the intra oral sensor device 100 is bent may be effectively relieved.

In this regard, the sensor panel 110, the elasticity adjustment member 120, and the PCB 130 are separate configurations having different properties, in particular having different tensile properties. Accordingly, while the intra oral sensor device 100 is bending, there occurs a difference in displacement between the different components, leading to the occurrence of tensile stress. In this case, with the soft adhesives 161, 162 used between the different components, the tensile stress may be effectively relieved.

In the meantime, taking into account all the various properties, it is preferable for the first adhesive 161 to be about 50 to 70 um thick and for the second adhesive 162 to be about 10 to 50 um thick.

Figure 9:
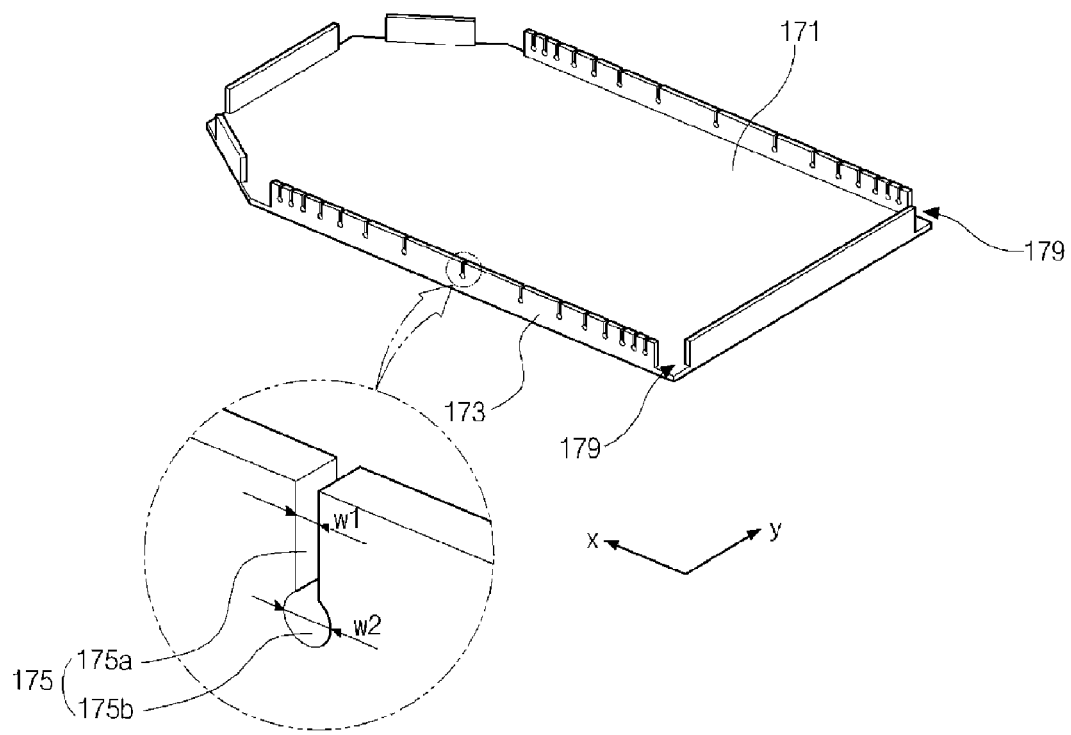
FIG. 9 is a perspective view schematically illustrating a window cover, according to an embodiment of the present invention.

FIG. 9 is a perspective view schematically illustrating a window cover according to an embodiment of the present invention.

Referring to FIG. 9 in conjunction with FIGS. 1, 2, and 3, the window cover 170 is located in front of the sensor panel 110 and is shaped like a box with the rear side open. The sensor assembly 105 may be contained in the internal space on the bottom face of the window cover 170.

The window cover 170 may be combined with the sensor panel 110 using an adhesive transparent to radiation. As the adhesive, for example, OCA or foam tape may be used, without being limited thereto.

The window cover 170 having such a structure may protect the sensor assembly 105, in particular the front of the sensor panel 110, against the external environment.

In particular, the window cover 170 in accordance with an embodiment of the present invention serves to define and limit the overall flexibility of the intra oral sensor device 100 depending on its material, shape, etc.

In this regard, the window cover 170 may be made of a highly bendable and high-strength material. For example, the window cover 170 may be made of flexible glass or FRP, like the elasticity adjustment member 120, but is not limited thereto. In addition, the window cover 170 may be about 0.1 to 0.5 mm thick, but is not limited thereto.

Because the window cover 170 is formed of such a material, the sensor assembly 105 may limit its bending to the range that falls within the flexibility of the window cover 170. This may prevent the sensor panel 110, which is a key component, from breaking when the sensor assembly 105 is excessively bent. Furthermore, since the intra oral sensor device 100 is bent within a limited range, the distortion of images may be minimized.

In addition, the window cover 170 may include a base part 171 and side walls 173 that orthogonally bend and protrude backwards from the edges of the base part 171.

The base part 171 may be formed to be substantially planar. Preferably, the side walls 173 may not be formed on the corners of the edges of the base part 171. In other words, the neighboring side walls 173 may be disconnected and separated on the corners of the base part 171, meaning that there may be gaps 179 between the neighboring side walls 173.

As such, the side walls 173, discontinuously formed along the edges of the base part 171 with some gaps 179 at the corners of the base part 171 where neighboring side walls 173 meet, may reduce the occurrence of structural resistance at the corners of the window cover 170 and may prevent the window cover 170 from breaking down due to the concentration of stress at the corresponding parts while the intra oral sensor device 100 is bending.

In the meantime, grooves 175 may be vertically formed in the side walls 173.

In this regard, more specifically, corresponding grooves 175 are formed in the two opposite side walls 173 located along the x-axis, the major axis for the rectangular window cover 170, and in particular, the intervals at which the grooves 175 are formed become narrower as the grooves 175 are located farther from the center of the corresponding side wall 173.

With the grooves 175 formed as described above, the extent of bending changes depending on the position along the x-axis. In other words, the narrower the intervals between the grooves 175, the more the corresponding part is bent; the wider the intervals between the grooves 175, the less the corresponding part is bent.

Accordingly, the window cover 170 has a property such that the extent of bending increases moving toward either end from the center along the x-axis, and such a property is applied to the intra oral sensor device 100.

As such, by adjusting the bending property according to the position, the patient's discomfort during an intra-intra oral scan may be more effectively relieved.

In other words, during the intra-intra oral scan, the end parts, rather than the center part, mostly come into contact with tissues in the mouth and cause pain. Therefore, increasing the flexibility of the end parts helps relieve the patient's discomfort. A part nearer the center part is characterized in that it is less bendable, which helps to minimize image distortion attributable to bending on the whole.

Although the grooves 175 are formed in the side walls 173 along the major axis in the above embodiment, the grooves 175 may be formed in the side walls 173 along the minor axis, if necessary, and the intervals between the grooves 175 may be adjusted.

The grooves 175 formed in the side walls 173 have a form such that they vertically extend from the top of the side wall 173. The grooves 175 may each include a first groove part 175a extending down from the top and substantially having a constant first width w1 and a second groove part 175b located below the first groove part 175a. At least a part of the second groove part 175b may be formed to have a second width w2, which is wider than the first width w1.

The second groove part 175b may have various forms, and in an embodiment of the present invention, it is assumed that the second groove part 175b may be shaped like a round circle.

As such, forming the second groove part 175b of the side wall 173 to have a relatively wide width w2 may help prevent the bottom part of the grooves 175 on the side walls 173 from breaking while the intra oral sensor device 100 is bending, and may widen the groove 175 while the intra oral sensor device 100 is bending, thereby improving its flexibility.

Unlike what is shown in the drawings, the grooves 175 may extend to a portion of the base part 171, in which case they still work the same way. Furthermore, if necessary, a plurality of extra grooves may be formed in at least one of the sides of the base part 171, i.e., in at least one of a side with which the sensor panel 110 comes in contact and the other side, in a direction perpendicular to the length direction of the intra oral sensor device 100, and the intervals between the extra grooves may also become narrower the closer they are located to the ends from the center. In this case, the extra grooves may not necessarily pass through the base part 171, and especially, may have a depth equal to or less than the thickness of the base part 171 when formed in the inner side of the base part 171, and may have a tapering form in which the intervals between the extra grooves become wider the nearer they are located to the outside of the base part 171.

Turning back to FIG. 2, the protective cover 180 may be located behind the PCB 130 and may be formed to be substantially planar, without being limited thereto.

The protective cover 180 may protect the components of the intra oral sensor device 100 from behind.

Furthermore, the protective cover 180 in accordance with an embodiment of the present invention may be formed to define and limit the overall flexibility of the intra oral sensor device 100 together with the aforementioned window cover 170.

For this, the protective cover 180 may be made of a low-elasticity, high-strength material, for example, polycarbonate (PC) having a thickness of 0.1 to 0.5 mm, without being limited thereto.

In addition, an opening 183 through which a transmission cable 210 passes may be formed in the center of the protective cover 180.

The transmission cable 210 is drawn in through the opening 183 in the protective cover 180 and is connected to the PCB 130.

The protective cover 180 and the PCB 130 may be formed to be separated from each other. Specifically, a separation gap 182 may be formed between the protective cover 180 and the PCB 130, and may be connected to the opening 183 to draw the transmission cable 210 into the separation gap 182 through the opening 183.

In this case, the separation gap 182 may be filled with a filler 220. The filler 220 may be filled up to the opening 183.

The filler 220 may use a resin that is hardened by heat or ultraviolet (UV) radiation, e.g., an epoxy resin. The filler 220 is injected into the separation gap 182, and is then hardened by heat or UV radiation.

As the separation gap 182 is filled with the filler 182, the electrical connection of the transmission cable 210 may be fixed more reliably.

In another example, an adhesive may be used to fill the separation gap 182, instead of the filler 182. The adhesive is a means to attach the PCB 130 and the protective cover 180 to each other, and with the adhesive, the transmission cable 210 may be reliably fixed to the PCB 130.

With the aforementioned components, the sensor panel 110, elasticity adjustment member 120, PCB 130, window cover 170, and protective cover 180 are modularized by being combined together. The intra oral sensor device modularized in this way may be covered with a mold housing 190.

The mold housing 190 is a means of enclosing the exterior of the modularized intra oral sensor device 100 for protection.

The mold housing 190 may be formed of a soft material, e.g., silicon or urethane. Especially, as the soft material for the mold housing 190, a material having a shore hardness of about A 30 to 50 may be used, without being limited thereto.

Moreover, the mold housing 190 may be formed to be, about 2 mm thick, taking into account its characteristics, without being limited thereto.

The use of the soft mold housing 190 may help greatly in relieving the pain felt by the patient during an intra-intra oral scan.

In other words, using a soft material for the mold housing 190, which is the outermost component of the intra oral sensor device 100 that comes into direct contact with intra-intra oral tissues, feels soft to the patient wearing the intra oral sensor device 100, thereby effectively relieving the pain felt by the patient.

The intra oral sensor device 100 covered with the mold housing 190 may have a thickness of about 5 mm or so, without being limited thereto, taking into account its characteristics.

The mold housing 190 may extend to also cover part of the transmission cable 210.

In this regard, the transmission cable 210 may include a wire for transmitting electric signals and a cover, i.e., a first cover for wrapping the wire with an insulating material, the wire wrapped with the first cover being extended to the outside of the intra oral sensor device 100. A first part, which is a part that extends a certain length from an end coming in contact with the PCB 130, is wrapped with an external cover, i.e. a second cover 211. The first part is defined from an inner part of the intra oral sensor device 100 to an outer part, and of the first part, a part located outside of the intra oral sensor device 100, i.e. located outside of the protective cover 180, is defined as a second part.

At least a part of the second part is formed to be wrapped by an extension 191 of the mold housing 190 that wraps up the intra oral sensor device 100. In the embodiment of the present invention, for convenience of explanation, it is assumed that the extension 191 of the mold housing 190 is formed to wrap the entire second part of the transmission cable 210.

With the mold housing 190 formed to extend to wrap a part of the transmission cable 210, the transmission cable 210 may be fixed to the intra oral sensor device 100 more firmly. Accordingly, more reliable electrical connection of the transmission cable 210 may be achieved.

The second cover 211 may be formed of a material from the same family to which the material of the mold housing 190 belongs. In this regard, for example, the second cover 211 may be formed of a silicon- or urethane-based resin material.

Forming the second cover 211 with a material from the same family to which the material of the mold housing 190 belongs may help improve the junction property between the mold housing 190 and the second cover 211, and as a result, may more reliably attach the transmission cable 210 to the intra oral sensor device 100.

The intra oral sensor device in accordance with the aforementioned embodiments of the present invention may be used as an intra-intra oral sensor inserted into the mouth of a patient and closely adhered to an intra-intra oral structure, i.e. the teeth and surrounding tissues, for an X-ray scan of the structure.

The intra oral sensor device bends differently at each position depending on adhesive force toward the structure and repulsive force from the intra-intra oral structure of the patient, and preferably, bends differently with the maximum crossing angle formed by two tangent lines tangential to maximum bending points at either edge along the major axis against the repulsive force in relation to arrangement of the structure, ranging from 90° to 180°, when a physical force is applied to the center of the rear side of the intra oral sensor device in the direction perpendicular to the length direction toward the structure while the intra oral sensor device is put in the mouth for an intra-intra oral X-ray scan.

Accordingly, a foreign feeling and pain that might be felt by the patient may be significantly relieved, and furthermore, image distortion is less likely to occur.

As described above, the intra oral sensor device in accordance with the embodiments of the present invention includes a window cover for containing and protecting a bendable sensor assembly as well as maximizing the bending property at its edges while being inserted into the mouth for an intra-intra oral X-ray scan. Accordingly, it is possible to implement the bendable intra oral sensor device to prevent breakage of a main part, namely the sensor panel, the minimize distortion of images, and ease the patient's discomfort to a significant extent.

For this, grooves may be formed in the wall of the window cover to control the bendable property, thereby minimizing the distortion of images and more efficiently relieving the patient's discomfort during an intra-intra oral scan.

Furthermore, a soft mold housing may be used to cover the exterior of the intra oral sensor device, thereby relieving the patient's discomfort to a significant extent during a scan.

Moreover, the mold housing may be extended to wrap part of the transmission cable, thereby achieving a reliable connection between the transmission cable and the intra oral sensor device.

Consequently, according to the present invention, an intra oral sensor device having a property of limited flexibility, which helps minimize image distortion, may be efficiently implemented, and in addition, may reliably protect a connection part between the transmission cable and the PCB, thereby minimizing the patient's discomfort.

The invention claimed is:

1. An intra oral sensor device comprising:
   a bendable sensor assembly for detecting an X-ray by a sensor panel and generating an electric signal; and
   a window cover covering the sensor panel with respect to a direction of X-ray propagation,
   wherein the window cover includes a base part contacting a bottom of the sensor panel and side walls protruding from edges of the base part to cover sides of the sensor panel, and
   wherein each of the side walls includes a plurality of grooves, the plurality of grooves are formed in the side walls arranged along a major axis of the window cover to control a bendability of the bendable sensor.

2. The intra oral sensor device of claim 1, wherein intervals between the grooves become narrower from a center of the side wall to either end thereof.

3. The intra oral sensor device of claim 1, wherein the window cover includes gaps formed between neighboring side walls on the edges of the base part.

4. The intra oral sensor device of claim 1, wherein the groove comprises a first groove part extending down from the top of the side wall and having a first width, and a second groove part located below the first groove part, at least a part of the second groove part having a second width greater than the first width.

5. The intra oral sensor device of claim 4, wherein the second groove part is shaped like a circle.

6. The intra oral sensor device of claim 1, wherein the window cover is formed of a FRP or a flexible glass material.

7. The intra oral sensor device of claim 1, wherein the sensor assembly includes a sensor panel for detecting the X-ray and generating the electric signal; a circuit panel located behind and connected to the sensor panel to deliver the electric signal; and an elasticity adjustment member located between the sensor panel and the circuit panel and formed of an elastic material having elasticity greater than that of the sensor panel and the circuit panel.

8. The intra oral sensor device of claim 1, further comprising: a protective cover to cover the sensor panel from behind the sensor panel with respect to the direction of X-ray propagation; and a mold housing to wrap the exterior of the intra oral sensor device.

9. The intra oral sensor device of claim 8, wherein the mold housing is formed of a material having a shore hardness of A 30 to 50.

10. The intra oral sensor device of claim 9, wherein the mold housing is formed of a silicon or urethane material.

11. An intra oral sensor device comprising:
    a bendable sensor assembly for detecting an X-ray by a sensor panel and generating an electric signal;
    a window cover covering the sensor panel with respect to a direction of X-ray propagation, and
    a mold housing wrapping the exterior of the intraoral sensor device,
    wherein the window cover includes a base part contacting a bottom of the sensor panel to protect the sensor and side walls protruding from edges of the base part to cover sides of the sensor panel, and
    wherein each of the side walls includes a plurality of grooves to control a bendability of the bendable sensor.

* * * * *